US006262054B1

(12) United States Patent
Fennelly et al.

(10) Patent No.: US 6,262,054 B1
(45) Date of Patent: *Jul. 17, 2001

(54) COMBINATION THERAPY METHOD FOR TREATING BREAST CANCER USING EDATREXATE

(75) Inventors: David William Fennelly; Francis Michael Sirotnak, both of New York, NY (US)

(73) Assignee: Sloan-Kettering Institute of Cancer Research, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/595,352

(22) Filed: Feb. 1, 1996

(51) Int. Cl.[7] .................... A61K 31/495; A61K 31/50; A61K 31/335
(52) U.S. Cl. .................................. 514/249; 514/449
(58) Field of Search ....................... 514/449, 249

(56) References Cited

U.S. PATENT DOCUMENTS

| | | | |
|---|---|---|---|
| 4,369,319 | 1/1983 | DeGraw, Jr. | 544/260 |
| 4,393,064 | 7/1983 | DeGraw, Jr. | 424/251 |
| 5,424,073 | 6/1995 | Rahman | 424/450 |
| 5,440,056 | 8/1995 | Klein | 549/510 |

FOREIGN PATENT DOCUMENTS

| 3843054 | 7/1989 | (DE) | C07K/7/64 |
|---|---|---|---|

OTHER PUBLICATIONS

D. Fennelly et al., "Phase I Trial of Sequential Edatrexate (TEX) following by Paclitaxl (PTX): A Design Based on In Vitro (IV) Synergy in Patients (PTS) with Advanced Breast Cancer," Thirty–first Annual Meeting of the American Society of Clinical Oncology May 20–23, 1995 Program/Proceedings, vol. 14, Mar. 1995, Los Angeles, California, p. A105.

Ting–Chao Chou et al., "Schedule–dependent Synergism of Taxol or Taxotere with Edatrexate Against Human Breast Cancer Cells In Vitro," *Cancer Chemother Pharmacol*, vol. 37, No. 3, 1996, pp. 222–228.

Andrew D. Seidman et al., "Memorial Sloan–Kettering Cancer Center Experience With Paclitaxel in the Treatment of Breast Cancer," *Seminars in Oncology*, vol. 22, No. 5, Suppl. 12, Oct. 1995, pp. 108–116.

D.T. Diamandidis et al., "Phase I Study of Taxol and Edatrexate (EDAM) Chemotherapy in Solid Tumors," Thirtieth Annual Meeting of the American Society of Clinical Oncology May 14–17, 1994 Program/Proceedings, vol. 13, Mar. 1994, Dallas Texas, p. A453.

Chou et al., "Combined effects of edatrexate with taxol against breast cancer cell growth," Proc. Am. Assoc. Canc. Res. Anmn. Mtg. V.34 (Abstract No. 1783) (1993).

Kris, et al.,"Phase I Trial and Clinical Pharmacological Evaluation of 10–Ethyl–10–deazaaminopterin in Adult Patients with Advanced Cancer ," *Cancer Research* 48 5573–5579 (1988).

Lee et al., "Edatrexate Improves the Antitumor Effects of Cyclophosphamide and Cisplation Against Non–Small Cell Lung Cancer," *Cancer* 68:959–964 (1991).

DeGraw et al., "New Analogs of Methotrexate in Cancer and Arthritis" *Current Medicinal Chemisty* 2:630–653 (1995).

Grant et al, "Edatrexate, an Antifolate with Antitumor Activity: A Review," *Cancer Investigation*, 11(1):36–45 (1993).

Schornagel et al., "Phase II study of edatrexate in chemotherapy–naive patients with metastatic breast cancer," *Annals of Oncology*, 3:549–552 (1992).

Sirotnak, et al., "10–Ethyl–10–Deaza–aminopterin: Structural Design and Biochemical, Pharmacologic, and Antitumor Properties," *NCI Monographs*, 5:127–131 (1987).

Seidman, "Single–agent use of TAXOL (paclitaxel) in breast cancer," *Annals of Oncology*, 5 (Suppl. 6):S–17–S–22 (994).

Kris et al., "Assessment of Pretreatment symptoms and improvement after EDAM+mitomycin–vinblastine(EMV)in patients (PTS) with inoperable non–small cell lung cancer (NSCLC)," *Proc. Am. Soc. Clin. Oncol.*, 9:229 (1990).

Fennelly et al., "Phase I Trail of Edatrexate Plus Paclitaxel Using an Adminstration Schedule with Demonstrated in vitro Synergy," *Lung Cancer*13:365 (1994).

Fennelly, et al., "Phase I trial of sequential edatrexate (etx) followed by paclitaxel (ptx): a design based on in vitro (IV) synergy in patients with advanced breast cancer," *Proc. Am. Assoc. Can. Res.*, 36:247 (1995).

Kingston et al., "Synthesis and Structure–Activity Relationships of Taxol Derivatives as Anticancer Agents," *Studies in Organic Chemistry*, 26:219–235 (1986).

*Primary Examiner*—Jerome D. Goldberg
(74) *Attorney, Agent, or Firm*—Dianne E. Reed; Mark A. Wilson; David W. Maher

(57) ABSTRACT

This invention provides combination therapy methods, pharmaceutical combinations and compositions for inducing tumor cell regression in cancer patients, particularly metastatic breast cancer patients. The combination methods, combinations and compositions employ both edatrexate and a taxane which are administered simultaneously or sequentially. The combination therapy described here permits the administration of unusually high doses of edatrexate.

20 Claims, No Drawings

COMBINATION THERAPY METHOD FOR TREATING BREAST CANCER USING EDATREXATE

FIELD OF THE INVENTION

This invention relates to a combination therapy of a taxane and edatrexate to treat various cancers, including breast cancer.

BACKGROUND OF THE INVENTION

Breast cancer is the most common malignancy among women and along with lung cancer has the highest fatality rate of all cancers affecting women. The search for new active agents and strategies to improve the prognosis for patients with metastatic breast cancer continues. In spite of the existence of numerous chemotherapeutic agents and regimens found to have antitumor activity, research continues in an effort to find improved treatment modalities, since survival rates in certain cancers remain low. For example, less than one in five patients with Stage IV (advanced) breast cancer survives more than five years after distant metastases are detected.

Methotrexate has been one of the standard anti-tumor agents in the treatment of breast cancer. Edatrexate (10-ethyl-10-deaza-aminopterin) is a relatively new structural analog of methotrexate which was developed at the Memorial Sloan-Kettering Cancer Center in New York in collaboration with SRI International. Like methotrexate, edatrexate inhibits dihydrofolate reductase. However, edatrexate is deemed a promising alternative because in preclinical tests it proved to have a greater antitumor activity than methotrexate against a number of tumors, partly attributed to the fact that this new analog accumulated in sensitive tumor cells to a greater extent than its predecessor methotrexate and was more selectively retained by the tumor cells. See, e.g. Kris et al., *Cancer Research* 48:5573–5579 (1988) and Sirotnak et al., *NCI Monographs*, No. 5 (1987).

The use of edatrexate as a single agent treatment against various tumors has met with some success. Studies of non-small cell lung cancer patients have reported positive results, with response rates being in the range of 30%. Grant et al., *Cancer Investigation* 11:36–45 (1993). Antitumor activity of edatrexate has also been observed in patients with non-Hodgkin's lymphoma, head and neck carcinoma, and breast cancer. (Vandenberg et al., *Proc. Am. Soc. Clin. Oncol.* 11:51 (1992); Schornagel et al., *Ann. of Oncology* 3:549–552 (1992). No anti-tumor activity was observed in patients with smallcell lung cancer or metastatic colorectal carcinoma. See Grant et al., supra, for a general review of clinical trials with edatrexate.

Edatrexate has also been tested to a certain extent with other various agents in patients with non-small cell lung cancer. For example, positive responses have been reported from the administration of edatrexate with mitomycin and vinblastine (Kris et al., *Proc. Am. Soc. Clin. Oncol.* 9:229 (1990) and with cisplatin and cyclophosphamide (Lee et al., *Cancer* 68:959–964 (1991). See, also, Grant et al., supra.

As with other chemotherapeutic drugs, dosages of edatrexate have been limited because of toxic effects of the drug. The primary toxic effect of edatrexate is mucositis, but leukopenia, thrombocytopenia and myelosuppression also occur. Due to side effects, dosages of edatrexate have been, prior to the invention described below, limited to a range of 80 mg/m$^2$ body surface area/week, with dosages of up to 120 mg/m$^2$/week given occasionally. Grant et al., supra, pages 42–44 and Schornagel et al., supra, p. 551. Fatigue, nausea and vomiting are also side effects of the drug, but severity of these events do not appear to correlate with dosage.

Another agent studied for the control of certain cancers is paclitaxel known as TAXOL®. Paclitaxel was first demonstrated to have activity against refractory ovarian cancer and has subsequently been found to have anti-tumor properties in some breast cancer patients. Seidman, *Annals of Oncology* 5 (Suppl. 6):S17–S22 (1994). The primary dose limiting toxic effect of paclitaxel is myelosuppression.

As with the multiple chemotherapeutic drugs available, neither edatrexate nor paclitaxel alone is curative for most metastatic breast cancer patients.

SUMMARY OF THE INVENTION

This invention provides novel combination therapy methods, pharmaceutical combinations and compositions for inducing tumor cell regression in cancer patients, particularly metastatic cancer patients. These methods employ regimens where cancer patients are treated concurrently with edatrexate and a taxane derivative, preferably paclitaxel, either simultaneously or sequentially. In cancer patients, for example, breast cancer patients, high patient response rates are seen with these treatments. The combination treatment of edatrexate with a taxane surprisingly permits the administration of unusually high dosages of edatrexate, i.e. about 180 mg/m$^2$ up to a dose of about 400 mg/m$^2$ without the degree of toxicity found when edatrexate is administered alone or with other agents. It was further surprising that such high dosages were effective without dose limiting side effects in light of preclinical test results in mice which indicated that the dosage of edatrexate and taxol should be reduced when the drugs are used together. The mouse data is presented below in Example 1.

Such combination treatments advantageously have application for patients who have chemotherapeutically refractory metastatic breast cancer. The combination treatment described here provides an alternative treatment with a relatively high response rate which will be beneficial to certain breast cancer patients. Further, the increased patient response levels and the lack of serious side effects seen with these combination treatments, will allow many more patients to become eligible for a bone marrow transplant program where they would not have otherwise been eligible. Bone marrow transplants are typically only available for patients showing a major response to therapy that does not markedly compromise normal host tissues, viz. bone marrow. The combination treatments described here will enable patients who have not responded to other treatments an opportunity for this treatment.

DETAILED DESCRIPTION

This invention provides for advantageous combination therapies for cancers, including metastatic breast cancer using regimens which employ administration of a taxane derivative in conjunction with a relatively high dose of edatrexate. The combination described herein provides a better response rate in metastatic breast cancer patients than either drug alone and surprisingly permits the administration of a high dose of edatrexate. The combination results in a surprising synergy which is beneficial to many patients in slowing or stopping tumor cell growth in vivo.

The patients to be treated with the combination therapy provided here are those that have been diagnosed with breast cancer, including metastatic breast cancer. Metastatic breast cancer includes, but is not limited to, those cancers occurring in the breast designated as scirrhous, infiltrative, papillary, ductal, medullary and lobular which have metastasized to other parts of the body, usually by direct extension and via the lymphatics and the bloodstream. Among the most common sites for metastases are the lungs and pleura, the skeleton and the liver. Distant spread of the disease is usually detected by lymph node biopsy or by x-ray surveys of the skeleton and chest or by liver and bone scans using radioactive isotopes.

One element of the combination therapy described is a taxane derivative. The taxanes are a family of terpenes, including, but not limited to paclitaxel and docetaxel (Taxotere), which were derived primarily from the Pacific yew tree, *Taxus brevifolia,* and which have activity against certain tumors, particularly breast and ovarian tumors. Paclitaxel is a preferred taxane. It is considered an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. The term "paclitaxel" includes both naturally derived and related forms and chemically synthesized compounds or derivatives thereof with antineoplastic properties including deoxygenated paclitaxel compounds such as those described in U.S. Pat. No. 5,440,056, herein incorporated by reference, and that sold as TAXOLD by Bristol-Myers Oncology. Chemical formulas for paclitaxel are known and can be found in the two previous cited references. For example, in addition to TAXOL®, other derivatives are mentioned in "Synthesis and Anticancer Activity of Taxol other Derivatives," D. G. I. Kingston et al., *Studies in Organic Chemistry,* vol. 26, entitled "New Trends in Natural Products Chemistry" (1986), Atta-ur-Rabman, P. W. le Quesne, Eds. (Elvesier, Amsterdam 1986), pp 219–235 are explicitly included here.

The taxane derivative may be administered in a manner found appropriate by a clinician in generally accepted efficacious dose ranges such as those described in the *Physician Desk Reference,* 48th Ed. (1994), Publisher Edward R. Barnhart, New Jersey ("PDR") for paclitaxel. In general, the taxane is administered intravenously at dosages from about 135 to about 300 mg/m$^2$, preferably from about 135 to about 175 mg/m$^2$, and most preferably about 175 mg/m$^2$. It is preferred that the dosages be administered over a time period of about 1 to about 24 hours, typically over a period of about 3 hours. Dosages can be repeated from 1 to about 4 weeks or more, preferably from about 2 to about 3 weeks.

Provided other formulations of paclitaxel may be tolerated by a patient, the drug may be administered in any other form such as by injection or oral forms. Liposome formulations, for example, have been described. See, e.g. U.S. Pat. No. 5,424,073, which is herein incorporated by reference.

The taxane derivative, preferably paclitaxel, will be administered in the same regimen with edatrexate. It is preferred that the taxane be administered at the same time as edatrexate or after edatrexate has been given to the patient, typically about 24 hours after edatrexate has been administered. However, the taxane may be administered before edatrexate as well.

Edatrexate (10-ethyl-10-deaza-aminopterin) is a methotrexate analog. Like methotrexate, edatrexate is an inhibitor of dihydrofolate reductase. The structure of edatrexate is shown in Kris et al., *Cancer Research* 48:5573–5579 (1988) and DeGraw et al., *Current Medicinal Chemistry* 2:630–653 (1995) both of which are incorporated by reference herein.

The drug was first formulated at Memorial Sloan-Kettering Cancer Center in New York in a collaboration as mentioned above and information regarding it is available there. Its formulation is also described in U.S. Pat. Nos. 4,369,319 and 4,393,064, and DeGraw et al., supra., and are herein incorporated by reference.

Under the combination therapies described here, edatrexate is administered to a patient in at least one dose of 180 mg/m$^2$ or greater, preferably from a dose of about 180 mg/m$^2$ up to about 400 mg/m$^2$, most preferably in a dose of about 350 mg/m$^2$. Though dosages may be given more frequently, such as weekly, if tolerated by the patient, it is preferred that dosages of edatrexate are repeated after a period of about 14 days and more preferably after a period of about 20 days. In one preferred regimen, edatrexate is administered at escalating doses. More preferably, edatrexate will be administered at a rate of one dose every three weeks for twelve weeks. If the patient responds to the treatment, the treatments will be repeated.

Edatrexate is administered most conveniently and effectively by intravenous methods. Edatrexate, however, may be available in other forms which will permit alternative modes of administration such as via injection or oral routes. Those too may be used in a similar manner.

As with the use of other chemotherapeutic drugs, the individual patient will be monitored in a manner deemed appropriate by the treating physician. Typically, no additional drug treatments will occur until, for example, the patient's neutrophil count is at least 1500 cells/mm$^3$. Dosages can also be reduced if severe neutropenia or severe peripheral neuropathy occurs, or if a grade 2 or higher level of mucositis is observed, using the Common Toxicity Criteria of the National Cancer Institute.

The combination therapy agents described here may be administered singly or in a cocktail containing both agents or one of the agents with other therapeutic agents, including but not limited to, immunosuppressive agents, potentiators and side-effect relieving agents. The therapeutic agents will preferably be administered intravenously or otherwise systemically by injection i.m., subcutaneously, intrathecally or intraperitoneally.

The pharmaceutical compositions of this invention which are found in combination may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like.

In therapeutic applications, the dosages of the agents used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur.

This invention further includes pharmaceutical combinations comprising a taxane derivative and a dose of edatrexate as provided above and kits for the treatment of breast cancer patients comprising a vial of the taxane derivative and a vial of edatrexate at the doses provided above.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications and publications cited herein are incorporated herein by reference.

EXAMPLES

Example I

Combination treatment in mice. The P388 lymphoidal tumor was transplanted intraperitoneally ($10^6$ cells/mouse) into B2D51 mice. The animals were randomized into control and treated groups after tumor implant. One day after transplant, the animals were treated intraperitoneally with either one of two folate analogues, edatrexate (EDX) or methotrexate (MTX), or paclitaxel (TXL) or a combination of folate analogue with paclitaxel on two different schedules (simultaneous or EDX or MTX 24 hr. before TXL). Therapy was repeated three times at four day intervals between each treatment.

The data show that this tumor was responsive to both folate analogues, with EDX being more effective than MTX. (See Table 1a). Combination therapy with either EDX or MTX with TXL required attenuation of dosage of the antifolate and taxane to avoid lethal toxicity. EDX with TXL was substantially more effective than MTX with TXL given on the same schedule of administration at the maximum tolerated dose for each combination. Finally, the response was the same when EDX but not MTX were given either simultaneously or on a sequential schedule. Simultaneous administration of MTX plus TXL was somewhat better than sequential administration. The therapeutic activity of MTX with TXL on either schedule was approximately the same as that obtained with EDX alone.

TABLE 1a

Therapy of the P388 Murine Tumor
with Folate Analogues and
Paclitaxel Alone or in Combination

| Agent $R_x$ | Maximum* Tolerated Dose (mg/kg) | Median Survival Time (days ± SEM) | Increased Life-Span (%) | Long-term Survivors (n/t) |
|---|---|---|---|---|
| — | — | 8 ± 1 | | 0/5 |
| EDX | 100 | 35 ± 4 | +338 | 1/5 |

TABLE 1a-continued

Therapy of the P388 Murine Tumor
with Folate Analogues and
Paclitaxel Alone or in Combination

| Agent $R_x$ | Maximum* Tolerated Dose (mg/kg) | Median Survival Time (days ± SEM) | Increased Life-Span (%) | Long-term Survivors (n/t) |
|---|---|---|---|---|
| MTX | 55 | 27 ± 3 | +238 | 0/5 |
| TXL | 18 | 16 ± 2 | +100 | 0/5 |
| EDX + TXL | 50 + 14 | >50 | > +525 | 4/5 |
| EDX → TXL | 50 + 14 | >50 | > +525 | 4/5 |
| MTX + TXL | 27 + 14 | 39 ± 4 | +388 | 2/5 |
| MTX → TXL | 27 ± 14 | 33 ± 3 | +312 | 1/5 |

*q4d × 3 ip. Animals randomized into control and treated groups after tumor implant.

Example II

Human clinical trials with combination therapy. A Phase I dose escalation trial was designed to enroll cohorts of 5 patients, with each cohort receiving the same dose of edatrexate, adjusted for body surface area, as a 1-hour intravenous infusion followed approximately 24 hours later by TAXOL® at 175 mg/m$^2$ infused intravenously over 3 hours. This dose regimen was repeated every 21 days provided patients demonstrated complete remission (CR), partial remission (PR), improvement (I) or no change (NC). CR is defined as showing no clinical evidence of tumor, by physical or radiological examination, PR is defined as ≧50% decrease in the sum of the product of the longest diameter and its longest associated perpendicular of the tumor, and NC is defined as not meeting the criteria of a complete or partial remission and without the development of new lesions. Patients were withdrawn from the study if there was evidence of progressive disease or unacceptable toxic effects. The original protocol included three dose levels of edatrexate, 180, 210 and 240 mg/m$^2$. When no dose limiting toxicity was observed the protocol was amended to include doses of 270, 300, 350 and 400 mg/m$^2$.

The stated objectives were (1) to establish the maximally tolerated dose (MTD) of edatrexate when given in combination with TAXOL®, (2) to determine the toxicities of the combination, and (3) to establish the noncomparative efficacy of the combination.

In addition, the data was reviewed in terms of the efficacy of the combination in anthracycline and methotrexate resistant patients. Breast cancer patients who failed on an anthracycline or methotrexate-containing combination chemotherapy regimen for metastatic disease or relapse within six months of anthracycline or methotrexate-containing adjuvant therapy were considered to be anthracycline or methotrexate resistant.

Results

A total of 36 women with metastatic breast cancer were enrolled in the study. There was excellent compliance of the patients with the following protocol entry criteria: confirmed diagnosis of metastatic disease (32/32 available charts), Karnofsky performance status of >70% (30/32 available charts), WBC>3000 cells/mm$^3$ (32/32), platelets ≧150,000 cells (32/32), creatinine ≦1.2 mg/dl, (32/32) total bilirubin ≦1.2 mg/dl (31/32), no radiation or chemotherapy in the previous three weeks (32/32), no previous TAXOL® (32/32). Patients were also to be limited to those who had one previous cytotoxic agent; 17 patients had received one, 3 patients had received two cytotoxic agents, 11 had received none, one was not determined.

Dose Escalation

Dose ascension continued until edatrexate was administered at a dose of 400 mg/m$^2$ to three patients. All three patients enrolled in the 400 mg/m$^2$ treatment cohort developed grade 3–4 mucositis. Thus, the maximally tolerated dose for edatrexate for the general patient population was generally considered to be less than 400 mg/m$^2$, preferably 350 mg/m$^2$. (Table 1b)

TABLE 1b

Summary of Enrollment/Toxicity

| Dose level (mg/m$^2$) | No. of patients | Toxicity | Adverse event |
|---|---|---|---|
| 180 | 6 | 0 | |
| 210 | 7 | 1/7 | leucopenia |
| 240 | 5 | 0 | |
| 270 | 5 | 0 | |
| 300 | 5 | 0 | |
| 350 | 5 | 0 | |
| 400 | 3 | 3/3 | grade 3—4 mucositis |

Previous Therapies/Disease Duration

The median duration of disease at the time of entry into this study was 2.8 years (range 0.1–10.2 years). A total of 76% (25/33) of the patients had received prior anthracycline (45%) or methotrexate (52%) containing chemotherapy. Five of these patients were considered to be anthracycline (n=4), methotrexate (n=1), or anthracycline and methotrexate (n=1) resistant. A total of 42% (14/33) of the patients received therapy with tamoxifen; 3 received that treatment alone, 9 received chemotherapy before or after the tamoxifen, and 1 received the tamoxifen treatment with radiation therapy. Thirteen patients (13/33 or 39%) received radiation therapy, all but one in conjunction with other therapies. Two patients, both in the 270 mg/m$^2$ treatment group had no previous therapies; one had a modified radical mastectomy, the other was newly diagnosed. Previous therapies are summarized in Table 2 as follows:

TABLE 2

Summary of Previous Therapy by Edatrexate Dose Group

| Dose level (mg/m$^2$) | N = | Anthracycline | Methotrexate | Tamoxifen | Radiation | None |
|---|---|---|---|---|---|---|
| 180 | 6 | 4 | 4 | 3 | 1 | 0 |
| 210 | 7 | 4 | 3 | 3 | 2 | 0 |
| 240 | 5 | 4 | 2 | 2 | 1 | 0 |
| 270 | 5 | 1 | 2 | 3 | 2 | 2 |
| 300 | 5 | 0 | 2 | 3 | 0 | 0 |
| 350 | 5 | 0 | 3 | 1 | 1 | 0 |

Although 45% (15/33) of the patients in the 180–350 mg/m$^2$ treatment groups received an anthracycline (Adriamycin) containing regimen all but four of these patients had not received these regimens within 6 months of recurrence. Similarly, 52% (17/33) of the patients in the 180–350 mg/m$^2$ treatment groups received a methotrexate containing regimen. All but one of these patients had not received these regimens within 6 months of recurrence of disease. These data are summarized in Table 3.

TABLE 3

Summary of anthracycline and methotrexate resistance

| Dose level (mg/m$^2$) | N = | anthracycline resistance | methotrexate resistance |
|---|---|---|---|
| 180 | 6 | 1 (183005/EP) | 1 (183005/EP) |
| 210 | 7 | 1 (196823/AB) | 0 |
| 240 | 5 | 1 (567874/AK) | 0 |
| 270 | 5 | 1 (332004/PB) | 0 |
| 300 | 5 | 0 | 0 |
| 350 | 5 | 0 | 1 (173383/AB) |

Summary of Clinical Response

Information regarding dose response efficacy can be gleaned from this study. The frequency of CR+PR was 5/6, 3/7, 2/5, 0/5, 2/5 and 3/5 for the 180, 210, 240, 270, 300 and 350 mg/m$^2$ treatment groups, respectively. Those patients who responded (CR or PR) were generally entered into a bone marrow transplant study. To qualify for this study they required thorough testing including, but not limited to CAT scan. Because of this, the likelihood of a false positive response in this study is low. Clinical response by treatment group is provided in Table 4.

TABLE 4

Summary of Clinical Response ALL PATIENTS

| Dose level | N = | Complete Remission | Partial Remission | No Change | Progression |
|---|---|---|---|---|---|
| 180 | 6 | 1 | 4 | 1 | 0 |
| 210 | 7 | 2 | 1 | 1 | 3 |
| 240 | 5 | 2 | 0 | 0 | 3 |
| 270 | 5 | 0 | 0 | 3 | 2 |
| 300 | 5 | 0 | 2 | 3 | 0 |
| 350 | 5 | 0 | 3 | 1 | 1 |
| TOTALS | 33 | 15/33 or 45% | | 9/33 or 27% | 9/33 or 27% |

Two of the five anthracycline and/or methotrexate resistant patients responded. Their results are summarized in Table 5 as follows:

TABLE 5

Summary of Clinical Response ANTHRACYCLINE (ANT)/METHOTREXATE (MTX) RESISTANT PATIENTS

| Dose level (mg/m$^2$) | Report No. | Hospital ID | Resistant to... | No. of Cycles | Clinical Response |
|---|---|---|---|---|---|
| 180 | 1 | 183005/EP | ANT/MTX | 4 | CR |
| 210 | 7 | 196823/AB | ANT | 6 | PR |
| 240 | 16 | 567874/AK | ANT | 2 | P |
| 270 | 21 | 332004/PB | ANT | 3 | P |
| 350 | 30 | 173383/AB | MTX | 4 | P |
| TOTAL RESPONSE | | | | | 2/5 or 40% |

The eight patients who had no prior cytotoxic chemotherapy are summarized in Table 6. Five of these patients had received prior tamoxifen with/without radiation therapy, one received radiation alone and two were newly diagnosed with metastatic breast cancer and were receiving their first therapy as part of this protocol. Two of these eight patients responded to the study regimen.

TABLE 6

Summary of Clinical Response
NO PREVIOUS CYTOTOXIC CHEMOTHERAPY

| Dose level $(mg/m^2)$ | Report No. | Hospital ID | No. of Cycles | Clinical Response |
| --- | --- | --- | --- | --- |
| 210 | 13 | 989030/VW | 4 | CR |
| 240 | 14 | 187193/BB | 2 | P |
| 270 | 19 | 328011/LM | 17 | NC |
| 270 | 22 | 936458/AN | 2 | NC |
| 270 | 23 | 334199/MG | 5 | NC |
| 300 | 24 | 791582/EC | 8 | NC |
| 300 | 28 | 333717/YK | 3 | NC |
| 350 | 29 | 330580 | 9 | PR |
| TOTAL RESPONSE | | | | 2/8 or 25% |

Twenty other patients had received previous cytotoxic chemotherapy containing anthracycline or methotrexate. There was a 55% response rate for this patient subset. (Table 7)

TABLE 7

Summary of Clinical Response
PREVIOUS CYTOTOXIC CHEMOTHERAPY

| Dose level $(mg/m^2)$ | Report No. | Hospital ID | No. of Cycles | Clinical Response |
| --- | --- | --- | --- | --- |
| 180 | 2 | 198280/CB | 5 | PR |
| 180 | 3 | 168664/DA | 10 | PR |
| 180 | 4 | 174837/EP | 12 | NC |
| 180 | 5 | 971560/MJ | 7 | PR |
| 180 | 6 | 175683/JS | 4 | PR |
| 210 | 8 | 960000/JS | 11 | NC |
| 210 | 9 | 170882/FF | 2 | P |
| 210 | 10 | 322338/LJ | 6 | CR |
| 210 | 11 | 174533/MR | 2 | P |
| 210 | 12 | 971835/SN | 6 | P |
| 240 | 15 | 943950/CN | 4 | CR |
| 240 | 17 | 194187/CJ | 4 | CR |
| 240 | 18 | 926183/HM | 4 | P |
| 270 | 20 | 197510/LD | 3 | P |
| 300 | 25 | 334445/BR | 4 | PR |
| 300 | 26 | 170601/BA | 6 | NC |
| 300 | 27 | 339717/CW | 5 | PR |
| 350 | 31 | 345525/MD | 8 | PR |
| 350 | 32 | 914202/MK | 5 | PR |
| 350 | 33 | 195868/MD | 5 | NC |
| TOTAL RESPONSE | | | | 11/20 or 55% |

Conclusions

The regimen of edatrexate followed within 24 hours by TAXOL® was acceptably well tolerated up to at least 350 mg/M$^2$ and improved the prognosis of a significant number of the patients. Some patients who were resistant to other chemotherapeutic agents responded under the combination therapies described above. Further, in a patient population which had been exposed to prior chemotherapy a high overall response rate of 55% was observed.

What is claimed is:

1. A method to induce enhanced regression of a tumor in a human breast cancer patient without side effects comprising administering to a patient having breast cancer a nontoxic dose of edatrexate of about 180 mg/m$^2$ up to about 400 mg/m$^2$ in a combination therapy with a nontoxic dose of a taxane derivative selected from the group consisting of paclitaxel, docetaxel and deoxygenated paclitaxel.

2. The method of claim 1, further wherein the taxane derivative is administered within 3 to about 24 hours after the edatrexate is administered.

3. The method of claim 1, further wherein about 135 mg/m$^2$ to about 175 mg/m$^2$ of the taxane derivative is administered after edatrexate is administered.

4. The method of claim 1, wherein the taxane derivative is paclitaxel.

5. The method of claim 1, wherein the taxane derivative is paclitaxel and is administered intravenously.

6. The method of claim 1, wherein the taxane derivative is paclitaxel and is administered intravenously together with the edatrexate.

7. The method of claim 1, wherein the dose of edatrexate is administered to the patient at a rate of one dose every three weeks.

8. The method of claim 1, wherein the taxane derivative is administered after the edatrexate, but within twenty-four hours of the edatrexate.

9. The method of claim 1, wherein the therapy further includes an immunosuppressive agent.

10. The method of claim 1, wherein the patient has metastatic breast cancer.

11. The method of claim 1, wherein the patient has not responded to a prior chemotherapeutic agent which was administered to the patient.

12. The method of claim 1, wherein the dose of edatrexate is about 240 mg/m$^2$.

13. A method to induce enhanced regression of a tumor in a human breast cancer patient without side effects comprising administering to said patient a pharmaceutically acceptable formulation of edatrexate at a nontoxic unit dosage of about 180 mg/m$^2$ or greater and concurrently administering to said patient a taxane derivative at a nontoxic unit dosage, wherein the taxane derivative is selected from the group consisting of paclitaxel, docetaxel and deoxygenated paclitaxel.

14. The method of claim 13, wherein the nontoxic dosage of edatrexate is about 180 to about 400 mg/m$^2$.

15. The method of claim 13, wherein the taxane derivative is paclitaxel.

16. The method of claim 14, wherein the nontoxic dosage of a taxane derivative is about 135 to about 300 mg/m$^2$.

17. The method of claim 16, wherein the taxane derivative is paclitaxel.

18. A method to induce enhanced regression of a tumor in a human breast cancer patient without side effects comprising administering to said patient a pharmaceutically acceptable formulation of edatrexate at a nontoxic unit dosage of about 180 mg/m$^2$ to about 400 mg/m$^2$ and concurrently administering to said patient paclitaxel at a nontoxic unit dosage of from about 135 mg/m$^2$ to about 300 mg/m$^2$.

19. A pharmaceutical combination for enhanced regression of a tumor in a human breast cancer patient without side effects comprising a unit dosage of edatrexate in an amount of about 180 mg/m$^2$ up to about 400 mg/m$^2$ and a nontoxic unit dosage of paclitaxel.

20. A pharmaceutical combination for enhanced regression of a tumor in a human breast cancer patient without side effects comprising a nontoxic unit dosage of a taxane derivative and a unit dose of edatrexate in an amount effective to provide edatrexate in a nontoxic unit dosage of about 180 mg/m$^2$ up to about 400 mg/m$^2$ to a human patient wherein the taxane derivative is selected from the group consisting of paclitaxel, docetaxel and deoxygenated paclitaxel.

* * * * *